(12) United States Patent
Palazzi

(10) Patent No.: US 11,925,603 B2
(45) Date of Patent: Mar. 12, 2024

(54) DRINKING STRAW WITH INTERNAL COATING

(71) Applicant: UNISTRAW CORP., Pepper Pike, OH (US)

(72) Inventor: Kendall Norman Palazzi, Singapore (SG)

(73) Assignee: UNISTRAW CORP., Pepper Pike, OH (US)

( * ) Notice: Subject to any disclaimer, the term of this patent is extended or adjusted under 35 U.S.C. 154(b) by 456 days.

(21) Appl. No.: 16/917,249

(22) Filed: Jun. 30, 2020

(65) Prior Publication Data
US 2020/0397659 A1 Dec. 24, 2020

Related U.S. Application Data

(63) Continuation of application No. 15/575,277, filed as application No. PCT/EP2016/063138 on Jun. 9, 2016.

(30) Foreign Application Priority Data

Jun. 10, 2015 (EP) ..................................... 15171534

(51) Int. Cl.
| | | |
|---|---|---|
| A61K 47/38 | (2006.01) | |
| A23L 2/52 | (2006.01) | |
| A23L 2/56 | (2006.01) | |
| A23L 2/58 | (2006.01) | |
| A23L 2/60 | (2006.01) | |
| A23L 27/00 | (2016.01) | |
| A23L 33/15 | (2016.01) | |
| A23L 33/16 | (2016.01) | |
| A23P 10/10 | (2016.01) | |
| A47G 21/18 | (2006.01) | |
| A61J 7/00 | (2006.01) | |
| A61K 9/00 | (2006.01) | |
| A61K 31/192 | (2006.01) | |

(52) U.S. Cl.
CPC .............. *A61J 7/0038* (2013.01); *A23L 2/52* (2013.01); *A23L 2/56* (2013.01); *A23L 2/58* (2013.01); *A23L 2/60* (2013.01); *A23L 27/70* (2016.08); *A23L 27/74* (2016.08); *A23L 33/15* (2016.08); *A23L 33/16* (2016.08); *A23P 10/10* (2016.08); *A47G 21/18* (2013.01); *A47G 21/183* (2013.01); *A61K 9/0095* (2013.01); *A61K 31/192* (2013.01); *A61K 47/38* (2013.01); *A23V 2002/00* (2013.01); *A47G 2400/105* (2013.01)

(58) Field of Classification Search
CPC .... A61K 9/0095; A61K 47/38; A61K 31/192; A47G 21/183; A47G 21/18; A47G 2400/105; A61J 7/0038; A23L 2/52; A23L 2/56; A23L 33/15; A23L 33/16; A23L 27/70; A23L 27/74; A23L 2/58; A23L 2/60; A23P 10/10; A23V 2002/00
See application file for complete search history.

(56) References Cited

U.S. PATENT DOCUMENTS

| | | |
|---|---|---|
| 4,981,468 A | 1/1991 | Benefiel et al. |
| 8,409,643 B2 | 4/2013 | Gaonkar et al. |
| 2004/0109932 A1* | 6/2004 | Chen ..................... A23G 3/36 426/660 |
| 2005/0089548 A1* | 4/2005 | Virgalitto ................ A23L 27/72 424/440 |
| 2005/0106188 A1 | 5/2005 | Sedaghat Kerdar et al. |
| 2006/0286214 A1 | 12/2006 | Weiss et al. |
| 2014/0084077 A1* | 3/2014 | Knight ................. A47G 21/183 239/33 |
| 2018/0133108 A1 | 5/2018 | Palazzi |

FOREIGN PATENT DOCUMENTS

GB      2 366 178      3/2002

OTHER PUBLICATIONS

Osorio et al. Characteristics of hydroxyl propyl methyl cellulose (HPMC) based edible film developed for blueberry coatings, Procedia Food Science 1, pp. 287-293 (Year: 2011).*
European Search Report & Written Opinion, EP Patent Application No. 15171534.9, dated Oct. 21, 2015.
International Search Report & Written Opinion, International Patent Application No. PCT/EP2016/063138, dated Aug. 23, 2016.

* cited by examiner

*Primary Examiner* — Johann R Richter
*Assistant Examiner* — Danielle Johnson
(74) *Attorney, Agent, or Firm* — Casimir Jones, S.C.; Tanya A. Arenson

(57) ABSTRACT

A drinking straw having an internal coating for delivery of an active agent when the straw is used to consume a beverage is provided. The active agent includes sweetener, flavour, a nutrient and/or a pharmaceutical and optionally colour. The coating is prepared by mixing a modified cellulose with water to form a paste or gel. The coating is then used to coat the inside surface of a drinking straw to a thickness of up to 1 mm. The coating is dried to reduce the water content to less than 5% by weight. Liquid drawn through the straw breaks down the modified cellulose releasing the active agent into the liquid, for consumption.

14 Claims, No Drawings

DRINKING STRAW WITH INTERNAL COATING

INTRODUCTION

The present invention relates to drinking straws having an internal coating which progressively dissolves, breaks down or erodes in a fluid being drawn through the straw in use. While the coating may typically include sweeteners and flavourings, it may additionally or alternatively include other agents such as vitamins, stimulants, probiotics and/or pharmaceutical products

BACKGROUND OF THE INVENTION

Filled straws are readily available in supermarkets around the world for adding flavour to beverages. The most commonly available straws are filled with pellets containing sweeteners and flavourings, for example strawberry or chocolate. The straws can be used to drink milk, with the pellets gradually dissolving in the milk as it is drawn through the straw, flavouring and sweetening the milk. The advantage of such straws are that a range of flavours take up less space, and they have a longer shelf life than flavoured milks, and are easier to use and more controlled than milk flavouring powder which has to be dissolved into milk to make a drink. Such straws can also be used to flavour water.

Other types of filled straws have also been proposed, in particular straws in which a dissolvable coating is adhered to the inside surface of the straw. As liquid is drawn through the straw in use, the coating dissolves into the fluid.

U.S. Pat. No. 4,921,713, in the name of Fowler, describes a straw for imparting flavour to otherwise neutral liquids, such as water or milk. Various methods of providing a material which dissolves in the liquid are described. These include a separate chamber containing flavouring material, granular material held within the body of the straw by a pair of sponges, and a flavouring material adhered to the inside of the straw.

US 2003/168772 in the name of Palaniappan describes a method of manufacturing an internally coated straw, in which the internal coating is applied to the inside of the straw as it exits the extruder in which it is formed. The coating material includes a matrix agent, which may be a maltodextrin or alginate, into which flavouring is added.

US 2011/143005, in the name of Gaonkar, also describes a drinking straw in which the inside of the straw is coated with a material that will flavour and sweeten a beverage drawn through the straw. The coating comprises an adhering agent and a powdered agent. The adhering agent includes lipids, medium chain triglycerides oils, emulsifiers, and mixtures thereof. The powdered agents include edible acids, edible bases, sweeteners, flavourings, vitamins, minerals, colorants, sensate agents, carotenoids, antioxidants, polyphenols, phytonutrients and mixture thereof.

The problem with all of these coatings is that the flavour they impart to the beverage is quite weak and/or they dissolve quickly in the beverage. Otherwise they are simply uneconomical to produce a commercial product.

US 2006/0286214, in the name of Sanford Weiss et al, describes an edible drinking straw comprising spirally wound layers of fruit film. The layers may be adhered together with a zein solution. This straw can be used to suck fluid into a user's mouth and as the fluid passes through the straw part of the straw dissolves imparting some flavour to the fluid. This will result in loss of structural integrity in the straw and once this has happened the remaining straw material can be dissolved into a fluid or eaten directly.

US 2005/0106188, in the name of Kerdar et al, describes a filled drinking straw in which the filling is retained within the straw by means of barrier devices which may be in the form of a plug or a mesh. These allow fluid to pass through the straw, dissolving the filling material, but retain any undissolved filling material within the straw. Other types of filled straw, for example EP1509096, are known in which the filling is provided in pellets and is retained in the straw by means of filters.

The provision of barrier means or filters adds additional steps to the manufacturing process, adding time and cost. In addition the barrier means or filters, unless integral to the straw, could become dislodged and represent a choking risk. In addition, failure of a filter, i.e. the creating of a larger aperture than intended, could result in the contents of the straw passing into the user's mouth undissolved, again representing a choking risk.

One of the objects of the invention is to provide a filled straw avoiding the use of barrier or filtration means.

US 2004/0109932, in the name of Chen et al, describes a coated drinking straw in which to coating comprises 40 to 99.99% of a food grade acid. The composition may also include a surface tension reducing agent, a plasticizer, a bulk agent and water. Coating may be via co-extrusion, spraying or dipping. A second coating may be provided in the form of a powder comprising further food grade acid, sugar, fizzing agents, colourants, probiotics, vitamins, herbs, and flavouring agents. This powder can adhere to the sticky surface of the acid coating.

It is desirable to provide a filled straw which provides an alternative to the pellet containing straws.

It is also desirable to provide a straw having an improved internal coating.

It is also desirable to provide a straw allowing consumption of a very thick or viscous beverage or a beverage that contains a high component of solid particles or a beverage that contains large solid or gel particles. These beverages will not pass through a straw that is filled with beads nor one that has a filter means at one or both ends. Examples of this are orange juice with pulp, semi-frozen beverages or bubble tea.

An object of the invention is to provide alternative drinking straws containing material which dissolves into a liquid drawn through the straw on use, and methods of making such straws.

SUMMARY OF THE INVENTION

A drinking straw is provided comprising an elongate body having an internal coating comprising a matrix which adheres to the inside of the body and holds agent to be consumed by a user.

DETAILS OF THE INVENTION

Accordingly, the present invention provides a drinking straw comprising an elongate tubular body of an insoluble material having an internal coating comprising a modified cellulose-based matrix containing an active agent dispersed within the matrix, the body sized to allow a carrier liquid to be drawn therethrough such that passage of the carrier liquid causes the matrix to progressively release the active agent into the carrier liquid to be consumed by a drinker, wherein the coating has a thickness of less than 1 mm.

In use, a user places one end of the straw into a container holding a beverage and draws the beverage through the straw, releasing active from the modified cellulose into the beverage for consumption.

Preferably the modified cellulose will be selected from hydroxypropyl methylcellulose, hydroxypropyl cellulose, methyl ethyl cellulose, methyl cellulose and carboxymethylcellulose or a combination thereof. All of these modified celluloses are approved for use in food use and as such have been given food additive numbers E464, E463, E465, E461 and E466. The preferred modified cellulose is hydroxypropyl methylcellulose.

The matrix is formed as a thick paste or gel which can adhere to the internal surface of the straw. The matrix is preferably formed as an aqueous paste or gel, and once it has been applied to the internal straw wall is optionally dried to remove excess water content. More preferably, the matrix is formulated to be non-drip; once applied such a matrix adheres to the internal straw wall without dripping or flowing and hence both does not drip and also does not flow so as to accumulate in vertically lower areas of the straw.

Usually the active agent will include sweetening and flavouring materials and may also include colorants. Such straws may contain acidulating materials. However, such straws may additionally or alternatively be used for delivery of other active agents, such as nutritional supplement, including herbal extracts, vitamins, minerals, amino acids, fatty acids, probiotics and/or pharmaceutical substances.

Where pharmaceutical, nutritional and/or vitamins and minerals are included in the active agent, sweeteners and/or flavourings may also be included.

Straws may also be formulated to provide an energy drink, the coating containing a stimulant, such as caffeine, and B vitamins. In such compositions it is important the water content be low as certain vitamins, and in particular B vitamins can degrade in the presence of water.

Straws containing any amino acids will also require a low water content as these compounds will also degrade in the presence of high moisture levels.

Usually the straws will be dried to have a water content of less than 5%, preferably less than 3% and most preferably less than 1% by weight.

Many pharmaceutical compounds can be provided in a form which may be held within the matrix and released into the liquid as the matrix breaks down or dissolves on passage of the liquid through the straw. The compounds may dissolve into the liquid, or may be suspended, but will be drawn into the user's mouth to be ingested. This may provide a more convenient form for some patients to take certain medications, as an alternative to swallowing tablets.

The active agent may also include nutritional compounds, which again may dissolved into the liquid or be suspended as the matrix dissolves into liquid drawn through the straw. Again this can provide a convenient way for such compounds to be taken.

The proportions of the matrix and the active agent may vary contingent on the active agent and the volume of liquid in which it is desired that the coating will dissolve. Typically a coating will comprise 5-30% by weight modified cellulose and 70-95% active agent. Preferably the modified cellulose will comprise 5-15% of the coating, and more preferably 10-15%. Typically the ratio of matrix to active agent will be between 1:2 and 1:20, more typically 1:5 and 1:20 and preferably between 1:5 and 1:10.

The coatings can be designed to dissolve in a predetermined volume of liquid, which will depend on the active agent and the user. Typically the coating will be designed to dissolve in 100-500 ml of liquid.

Coatings which comprise a pharmaceutical substance may be designed to dissolve in a relatively small volume of liquid, typically 100-150 ml, so that they can be consumed quickly and easily by the user, who may be ill.

Coatings which comprise mainly sweetening and flavourings, possibly additionally including vitamins and minerals, may be designed to dissolve over a larger volume of liquid, for example 250-500 ml, so that the user may enjoy a larger volume of flavoured beverage.

The thickness of the coating will also affect the dissolution of the coating. Thicker coatings will typically take longer to dissolve (at the same dryness level). Coatings will typically be applied to a thickness of up to 1 mm, e.g. 0.1-1 mm, more typically up to 0.7 mm, e.g. 0.2 to 0.7 mm. Usually the coating will have a thickness of up to 0.5 mm, preferably up to 0.25 mm. The most preferred thickness for the coating, used in a specific example below, is substantially 0.2 mm.

The combination of the thickness of the coating and the proportion of the matrix can be altered to vary the dissolution time and the strength of the active agent in the consumed beverage. For example a thin layer with a high proportion of matrix, say 30%, will dissolve slowly, and release the active agent slowly. This may be suitable where the active agent includes a very potent flavouring and sweetener, and small amount of these may be sufficient to flavour the liquid.

Alternatively a thicker layer of a coating comprising less matrix, say less than 10% will deliver more active agent over substantially the same volume of liquid drawn through the straw. This may be suitable where the flavour is less strong and it is necessary to deliver more.

In another embodiment, a thin layer of a coating comprising less matrix, can be used to deliver the active agent quickly, in less volume of liquid drawn through the straw. For example where the active agent to be delivered is a pharmaceutical product, the user may wish to consume this in a relatively small volume of liquid.

As discussed above, the water content of the coating may be relevant to the stability of the active agent. Typically the coated straw will be dried to remove additional water and reduce the water content. Usually the straws will have a water content of less than 5%, preferably less than 3% and most preferably less than 1% by weight.

The present invention also provides a method of preparing a drinking straw having an at-least partially coated internal portion, the method comprising the steps of:
  providing a drinking straw of an insoluble material;
  providing a coating material comprising a modified cellulose-based matrix and an active agent dispersed within the matrix;
  applying the coating to an internal surface of the drinking straw to a thickness of less than 1 mm; and
  drying the coating.

Preferably the modified cellulose will be selected from hydroxypropyl methylcellulose, hydroxypropyl cellulose, methyl ethyl cellulose, methyl cellulose and carboxymethylcellulose or a combination thereof. All of these modified celluloses are approved for use in food use and as such have been given food additive numbers E464, E463, E465, E461 and E466. The preferred modified cellulose is hydroxypropyl methylcellulose.

In some embodiments the coating is suitably prepared as a gel to enable adherence to the inside of the straw. In other embodiments it is prepared as a paste, typically a thick paste.

It is also preferably formulated to be non-drip so as to stay in place while drying, and not to run.

The coating may be prepared by mixing modified cellulose with water and heating the mixture to form a gel. The mixture may then be cooled before the active agent is added. Alternatively the coating may be prepared by mixing the modified cellulose with water and stirring to form a paste. Typically the paste may have a consistency of thick cream, whereby it can support its own weight and thus will not drip or run, in particular when spread on a surface.

A suitable coating mixture will typically contain 1-10 g modified cellulose, preferably 2-7 g and more preferably 2-4 g in 10 ml of water. The amount of water will be chosen with respect to the particular modified cellulose to achieve a non-drip material. An optional stage of gel formation may be carried out by heating and a suitable temperature may be 40-45° C., preferably 42° C.

While the active agent may be added while the matrix gel is at elevated temperature, usually the gel is cooled to substantially room temperate, namely 20-25° C. before the active agent is added. Where the matrix is not heated, no cooling is necessary.

Depending on the active agent and the volume of liquid into which the coating is designed to dissolve, typically 5-30 g, preferably 10-20 g and more preferably 10-15 g, of active agent will be added to the gel. The active agent will often include sweetener, for example steviol glycosides, or sugars including glucose and/or fructose, and may also include flavourings, for example fruit flavours, chocolate flavours, vanilla flavours. Colorants are also often included. Additionally or alternatively the active agent may also include pharmaceutical products such as analgesics or other medicaments. The active agent may also include nutritional compounds, including vitamins and minerals, and possibly fatty acids, amino acids, and/or phytochemicals. Alternative agents may include herbal extracts.

Typically the ratio of matrix to active agent will be between 1:2 and 1:20, more typically between 1:5 and 1:20 and preferably between 1:5 and 1:10.

Once the coating has been formed, it is used to at least partially coat the inside of a straw. Generally the straw will be made of plastic, typically polypropylene, although other types of plastic, for example polyethylene, or PET may be used. Metal or glass may also be used. Advantageously the straw may be provided as recyclable.

The coating may be applied by spraying the coating onto the inside of the straw. Alternatively it may be made by dipping the straw into the coating and wiping the excess off the outside.

Preferably the coating is applied using a mandrel, having a head 0.1 mm-1 mm smaller than the internal diameter of the straw. A predetermined amount of the coating is placed on the end of the mandrel which passed down the straw, depositing the coating as a thin layer around the internal circumference of the straw. In an alternatively the mandrel may be provided with a hollow body with an outlet on the head, the head having larger diameter than the body. A predetermined amount of coating can be pumped through the body to the head as the mandrel is passed down the straw. As the mandrel is returned out of the straw, the head smooths the coating evenly onto the inside of the straw. The relative size of the internal diameter of the straw and the diameter of the head of the mandrel determining the thickness of the coating applied.

The coating may be applied along the full length of the straw. In the alternative the coating may be applied to a portion of the length of the straw only. For example the coating may be applied to a middle section of the straw only, with no coating being applied adjacent one or both ends of the straw. A 10-30 mm end of the straw may be without coating. When the coating is applied using a spray, both ends of the straw may be without a coating. When a mandrel is used, typically one end only will be without coating. Alternatively the coating may be applied the full length of the straw and then removed from one or both ends, for example by washing or wiping.

The coating may also be applied to a portion of the straw to achieve a specific geometry relative to the beverage to be consumed. This may mean applied to the upper half of the straw for a coating that does not sit in the beverage being consumed or alternatively applied to the lower half of the straw for a coating that gives an improved result by sitting immersed in the beverage being consumed. In straws where the coating is applied unevenly, i.e. mostly in one half, usually the straw will be marked in some way to indicate to a user which end of the straw should be place in the beverage, and which should be used to drink through. This may be providing the straw with a flat end, possibly a rolled end, for drinking through, and an angled end to be placed in the beverage. Alternatively, the end to be placed in the drink may be flared. In a further alternative the outside of the straw may be provided with the indication, for example writing or colour coding.

Typically the coating will be applied to at least 50%, preferably at least 70% of the internal surface area of the drinking straw, preferably between 70 and 90% of the surface, and most preferably between 75 and 85% of the internal surface.

Once the coating has been applied, the coating is usually dried before the straw is packaged. Typically this is achieved by passing a stream of relatively cool, dry air, for example dry, room temperature air, through the straw. Alternatively coated straws may be passed through a moderately heated environment, or a flow of moderately heated air may be used to effect drying of the coating. Typically the air is not so hot as to cause melting of the straw or degradation of the active agent.

In may be advantageous to rotate the straw while applying the coating, and/or while drying the coating. This may assist in providing an even coating and achieving an even and complete drying of the coating.

Once dried the coating will typically have a water content of less than 5%, preferably less than 3% and most preferably less than 1% by weight.

After the drying the straws are typically packaged, either singly or in small numbers, typically 3-5, in a moisture impervious packaging material, to prevent the coating absorbing moisture from the atmosphere.

EXAMPLES

The invention is now illustrated in specific examples below.

Example 1

Drinking Straw with Lime Flavoured Coating

A coating for a drinking straw was prepared as follows:
5 g of hydroxypropyl methylcellulose was mixed with 10 g of water and the mixture heated to 42° C. to form a gel. The gel was cooled to room temperature, namely 20° C.

A flavour mix was prepared of 60 g of lime flavour, 5 g steviol glycosides, 5 g citric acid, and 0.4 g (4 drops) green colorant. 15 g of this mixture was added to the cooled gel to create a coating for drinking straws.

The coating was applied to the inside of 10 drinking straws. The straws had an 8 mm external diameter, a 7.6 mm internal diameter and were 22 cm in length. The coating was applied to the straw at a thickness of 0.25 mm using an appropriately sized mandrel. The coating was applied leaving a coating-free area at one end of 2 cm.

The coating was dried by passing cool, dry air through the straws for a period of 3 hours.

After drying the straw were wrapped in moisture resistant barrier packaging.

Such a straw was used to flavour water at 0° C. and provided flavour to approximately 350 ml consumed over a period of 10 minutes. Flavour was provided to the drink throughout that time with a residue only being left on the inside of the straw once the drink had been consumed.

Example 2

Drinking Straw with Chocolate Flavour Coating and Multivitamins

A coating was prepared by mixing 2 g of methylcellulose with 8 g water and the mixture stirred to form a thick paste.

Active agent was prepared by mixing 100 g chocolate flavour, 20 g glucose, 20 g of a commercial available multivitamin and mineral mix including vitamin C and a blend of B vitamins, calcium and iron.

15 g of this active agent mixture was then added to the gel and combined, and this coating mixture was used to coat 30 straws, as described with reference to Example 1. The coating was applied to a thickness of 0.2 mm and the straws were dried also as set out above to a final water content in the coating of less than 2% by weight.

One advantage of providing vitamins for consumption in this form is that certain vitamins, in particular B vitamins, degrade in water. By providing them in a coating in a straw they are provided in a dry environment.

This straw is used to drink milk and provide favour to 200-300 ml of milk at 5° C. when consumed over approximately 10 minutes.

Example 3

Drinking Straw with Analgesic Coating

An active agent mix was prepared by mixing 40 g ibuprofen with 5 g steviol glycosides, and 5 g mint flavour. 5 g of this mixture was added to a paste as described in Example 2 but using carboxymethylcellulose.

This mixture was used to coat 20 straws of the dimensions set out in Example 1, to a thickness of 0.2 mm.

The straws were then dried by passing cool air through them for a period of 1 hour. They were then wrapped in moisture resistant barrier packaging.

Such straws release the active agent into approximately 100 ml of water at room temperature, consumed over a period of 2 minutes.

Example 4

Drinking Straw with Energy Coating

An active agent mix was prepared by combining 5 g of a vitamin pre-mix containing vitamins B1, B2, B3, B6, B12 and M-Inositol, 2 g of caffeine, 3 g of steviol glycosides, 16 g of lime flavour and 12 g of citric acid. 15 g of this mix was added to the hydroxypropyl methyl gel as described with reference to Example 1.

This mixture was used to coat 15 straws, which were then dried by passing cool air through them for a period of 3 hours, until the water content was reduced to less than 1%. The coating was applied to the straw at a thickness of 0.2 mm using an appropriately sized mandrel.

The straws were then wrapped in moisture impervious packaging.

Such a straw was used to flavour water at 20° C. and provided flavour to approximately 250 ml consumed over a period of 10 minutes.

The invention hence provides internally coated drinking straws with coating comprising a matrix and an active agent, and methods of making the same.

The invention claimed is:

1. A drinking straw comprising an elongate tubular body of an insoluble material, having an internal coating adhered thereto consisting essentially of a mixture of (i) hydroxylpropyl methylcellulose, (ii) citric acid, and (iii) one or more active agents, the body being sized to allow a carrier liquid to be drawn therethrough such that the passage of the carrier liquid causes the mixture to progressively release the one or more active agents into the carrier liquid for consumption by a drinker.

2. The drinking straw of claim 1, wherein the coating has a water content of 5% or less.

3. The drinking straw of claim 1, wherein the one or more active agents is selected from the group consisting of a sweetener, a flavouring, a nutrient, a pharmaceutical and mixtures thereof.

4. The drinking straw of claim 1, wherein the coating has a thickness of up to 0.5 mm.

5. The drinking straw of claim 1, wherein the drinking straw is made of plastic.

6. A drinking straw comprising an elongate tubular body of an insoluble material, having a dried, aqueous internal coating adhered thereto consisting essentially of an intimate mixture of a modified cellulose material, an acidulating material and one or more active agents, the body being sized to allow a carrier liquid to be drawn therethrough such that the passage of the carrier liquid causes the mixture to progressively release the one or more active agents into the carrier liquid for consumption by a drinker.

7. The drinking straw of claim 6, wherein the acidulating agent is citric acid.

8. The drinking straw of claim 6, wherein the modified cellulose material is hydroxylpropyl methylcellulose.

9. The drinking straw of claim 6, wherein the coating has a water content of 5% or less.

10. The drinking straw of claim 6, wherein the one or more active agents is selected from the groups comprising a sweetener, a flavouring, a nutrient, a pharmaceutical or mixtures thereof.

11. The drinking straw of claim 6, wherein the one or more active agents comprises at least one of a sweetener or a flavouring.

12. The drinking straw of claim 6, wherein the coating has a thickness of 0.2-0.7 mm.

13. The drinking straw of claim 6, wherein the coating has a thickness of up to 0.5 mm.

14. The drinking straw of claim 6, wherein the drinking straw is made of plastic.

* * * * *